United States Patent
Plotz et al.

(10) Patent No.: US 8,809,255 B2
(45) Date of Patent: Aug. 19, 2014

(54) LOW VOC CONTENT WATERLESS CLEANER AND ARTICLE IMPREGNATED THEREWITH

(71) Applicants: Chris J. Plotz, Olathe, KS (US); Paul J. Gottesburen, Lawrence, KS (US)

(72) Inventors: Chris J. Plotz, Olathe, KS (US); Paul J. Gottesburen, Lawrence, KS (US)

(73) Assignee: Illinois Tool Works, Inc., Glenview, IL (US)

( * ) Notice: Subject to any disclaimer, the term of this patent is extended or adjusted under 35 U.S.C. 154(b) by 0 days.

(21) Appl. No.: 13/709,116

(22) Filed: Dec. 10, 2012

(65) Prior Publication Data

US 2013/0180066 A1 Jul. 18, 2013

Related U.S. Application Data

(60) Provisional application No. 61/585,763, filed on Jan. 12, 2012.

(51) Int. Cl.
*C11D 3/44* (2006.01)

(52) U.S. Cl.
USPC ........... 510/438; 510/130; 510/138; 510/157; 510/159; 510/295; 510/371; 510/417; 510/432

(58) Field of Classification Search
USPC ......... 510/130, 138, 157, 159, 295, 371, 417, 510/432, 438
See application file for complete search history.

(56) References Cited

U.S. PATENT DOCUMENTS

| | | | | |
|---|---|---|---|---|
| 5,666,628 | A * | 9/1997 | Fukai | 399/340 |
| 6,165,962 | A * | 12/2000 | Kaler et al. | 510/365 |
| 2007/0093404 | A1 * | 4/2007 | Gross et al. | 510/407 |
| 2009/0281012 | A1 * | 11/2009 | Trivedi et al. | 510/138 |
| 2012/0028875 | A1 * | 2/2012 | Kordosh | 510/405 |
| 2012/0129756 | A1 * | 5/2012 | Sehgal et al. | 510/417 |
| 2012/0137449 | A1 * | 6/2012 | Ransom et al. | 12/146 B |
| 2012/0149626 | A1 * | 6/2012 | Fluck et al. | 510/365 |
| 2012/0231987 | A1 * | 9/2012 | Britton | 510/138 |

* cited by examiner

*Primary Examiner* — Charles Boyer
(74) *Attorney, Agent, or Firm* — Blue Filament Law PLLC; Avery N. Goldstein

(57) ABSTRACT

A composition is provided that includes 0.5 to 15 total weight percent of a surfactant. The surfactant is a non-ionic surfactant, an anionic surfactant, or a combination thereof. The composition also includes 0.01 to 35 total weight percent of solvent including a microemulsion, a carboxylic acid ester based ketal ester solvent, or a combination thereof 0.1 to 10 total weight percent of at least one emollient, and 60 to 99.3 total weight percent of water also being present. The resultant composition has total volatile organic content (VOC) composition of less than 2 total weight percent and as a result, the composition is more environmental benign and less irritating to skin than conventional waterless hand cleaners. The composition is well suited for being impregnated into a substrate of a towel presenting two opposed surfaces, the substrate having pores for absorbing and retaining the composition.

4 Claims, No Drawings

LOW VOC CONTENT WATERLESS CLEANER AND ARTICLE IMPREGNATED THEREWITH

RELATED APPLICATIONS

This application is a non-provisional application that claims priority benefit of U.S. Provisional application Ser. No. 61/585,763 filed on 12 Jan. 2012; the contents of which are hereby incorporated by reference.

FIELD OF THE INVENTION

The present invention in general relates to a cleaning composition for removal of lipophilic substances such as paints, resins, oils, and organic soils from skin and hard surfaces, and in particular to waterless cleaning composition for doing so with low VOC content.

BACKGROUND OF THE INVENTION

Waterless hand cleaners routinely have a gelatinous consistency. These cleaners often have both hydrophilic and hydrophobic components which are blended together to affect removal of a wide variety of soils from the skin surface. While the gelatinous hand cleaner is effective in removal of material from the skin surface, subsequent water washing is invariably required to remove the residual debris filled gel. Additionally, a gel independent of an abrasive is often slow in removing substance from the skin surface. Conventional waterless cleaning compositions often contain as much as 45% by weight of organic solvents and high loadings of emulsifiers in order to solubilize grease and soil. These compositions require high concentrations of organic solvents and emulsifiers to remove hydrophobic materials through dual actions of emulsification and solvation.

Low viscosity, liquid waterless hand cleaners have proven popular and effective when used in conjunction with an abrasive article that retains the liquid in contact with the skin surface and provides mechanical action to disrupt soil or grease films on the skin surface. Representative of such products are those detailed in U.S. Pat. No. 5,683,971 in which an abrasive coated towel retains the cleaning composition.

Regardless of the viscosity, these conventional cleaning compositions have fallen out of favor owing to the high loading of organic solvents and emulsifiers that end up in wastewater, as well as the skin irritation associated with the use of such products. Volatile organic compound content (VOC) in consumer products is now tightly regulated and the acceptable limits of VOCs in such products are constantly being lowered. The high concentration of organic solvents and emulsifiers present in these conventional cleaner also makes subsequent removal of the cleaner difficult, often resulting in a residual film that retains soil and/or grease while the film tends to dry and irritate the underlying dermis. Owing to the environmental impact, cost, and skin irritation caused by contact with cleaner residue, there is a desire to reduce the usage of such solvents without compromising the cleaning ability of such waterless hand cleaners.

Thus, there exists a need for a cleaning composition that is amenable to impregnation into an article that has reduced ecotoxicity and improved skin compatibility while remaining effective against soils and greases.

SUMMARY OF THE INVENTION

A composition is provided that includes 0.5 to 15 total weight percent of a surfactant. The surfactant is a non-ionic surfactant, an anionic surfactant, or a combination thereof. The composition also includes 0.01 to 35 total weight percent of solvent including a microemulsion, a carboxylic acid ester based ketal ester solvent, or a combination thereof 0.1 to 10 total weight percent of at least one emollient and 60 to 99.3 total weight percent of water is also present. The resultant composition has total volatile organic compound content (VOC) is less than 2 total weight percent and is more environmental benign and less irritating to skin than conventional waterless hand cleaners.

The composition is well suited for being impregnated into a medium of a towel presenting two opposed surfaces, the substrate having pores for absorbing and retaining the composition. An abrasive ingredient adhered to at least one of the two opposed surfaces at least one said surface to facilitate mechanical removal of substances from the skin surface of a user.

DETAILED DESCRIPTION OF THE PREFERRED EMBODIMENTS

The present invention has utility as a free flowing, liquid cleaning composition especially well suited for removal of paint, resin, oils, and lipophilic soils from the skin surface with a low VOC content or no VOC content. The inventive cleaning composition is particularly well suited as a hand cleaner for removing such substances and soils from a user's skin in combination with a towel, such as that detailed in U.S. Pat. No. 4,833,003. The inventive composition is optionally pre-wet and impregnated into the article. Such wet articles are amenable to packaging in a container as a pre-perforated roll or stack of such articles that can be dispensed, used and discarded to affect cleaning without resort to a secondary water washing or cleaner removal. By reducing the VOC content of an inventive composition relative to the prior art, the environmental impact of the product is reduced along with the residual skin irritation.

As used herein, a VOC is defined as a compound listed on the United States Environmental Protection Agency Volatile Organic Compounds Master List.

An inventive composition is able to replace in part, or total regulatory controlled VOCs and still remain effective at removing lipophilic soils and greases through reliance on with from 0.1 to 35 total weight percent of a non-VOC microemulsion or 0.01 to 35 total weight percent of a non-VOC ketal ester, of a combination thereof with a combined loading of 0.1 to 35 total weight percent to replace in whole or part conventional waterless hand cleaner VOCs such as mineral spirits, limonene, and dibasic esters. The inventive composition also contains water present from 60 to 99.7 total weight percent; a surfactant of non-ionic or anionic type; along with optional additives forms a superior liquid cleaning composition; alone or when used in combination with a cleaning article. It is appreciated that all or part of the inventive solvent is replaced with vegetable oils, terpenes, or a combination thereof with the proviso that the VOC content remains below 5 total weight percent and preferably below 1 total weight percent.

The present invention reduces VOC content, skin irritation, and has storage stability while maintaining conventional cleaning properties with respect to paints, resins, and other lipophilic soils. Through selection of specific additives, antibacterial treatment is achieved and skin quality is also improved.

The formulary of an inventive cleaning composition is summarized below in Table 1.

TABLE 1

Inventive Cleaning Composition

| Component | Typical Amount Total Wt. Percent | Pref. Amount - Total Wt. Percent |
|---|---|---|
| Surfactant (non-ionic/anionic)* | 0.5-15 | 1-5 |
| Solvent (in total): | 0.01-35 | 1-6 |
| (a) Microemulsion, or | 0.1-35 | 1-4 |
| (b) Non-VOC ketal ester, or | 0.01-35 | 3-6 |
| Combination (a) + (b) | 0.11-35 | 1-5 |
| Emollients (alkylene glycol, glycerine, vitamin E acetate, dimethicone, lanolin, mineral oil, wheat germ extract, jojaba extract, etc., and combinations thereof) | 0.1-10 | 1-6 |
| Water | to 100% | to 100% |
| Optional components | | |
| Fragrance | 0-3 | 0.01-3 |
| Dye | 0-3 | 0.01-3 |
| pH adjustment additives (caustic, citric acid, etc.) | none - Ph = 13 | 0 |
| Polyvalent metal ion salt | 0-2 | 0-2 |
| Antimicrobial | 0-2 | 0.005-1 |
| Foaming agent | 0-2 | 0-0.6 |
| Polar organic solvent | 0-15 | 0.1-3 |
| Emulsifier | 0-10 | 1.2-8 |
| VOCs in total | 5< | 1< |

*exclusive of surfactant loading in microemulsion, if present

The inventive composition includes a non-ionic surfactant illustratively including fatty alcohols, polyoxypropylene glycol alkyl ethers, glycerol alkyl esters, and the like; an anionic surfactant illustratively including an alkyl sulfate, alkyl benzene sulfonate, alkyl ether phosphate, alkyl carboxylates, and the like; or a combination thereof. Preferably, a non-ionic surfactant is $C_{12}$-$C_{15}$ alkyl ethoxylated alcohol having an average degree of ethoxylation of from 3 to 7.

The inventive composition includes of a solvent that is a microemulsion, a non-VOC ketal ester or a combination thereof. A microemulsion is present at a total weight percent of between 0.1 and 35 percent and preferably between 1 and 4 total weight percent. More preferably, the microemulsion is present from 1.7 to 3.8 total weight percent. A microemulsion is preferably premixed and provided as a concentrate that is intermixed with the remaining composition constituents. Most preferably, the microemulsion is a dibasic ester microemulsion. Representative dibasic esters for an inventive microemulsion component are dimethyl-2-methyl glutarate, diesters of succinates and adipates, or a combination thereof. A preferred microemulsion operative herein includes an anionic surfactant that is water soluble and non-soaping and includes an organic hydrophobic group containing between 8 and 26 carbon atoms and preferably between 8 and 20 aliphatic carbons along with at least one hydrophilic moiety of hydroxyl, sulfonate, sulfate, or carboxylate. Hydrophobic portion of molecule typically includes a $C_8$-$C_{22}$ alkyl, aryl, or acyl group. The surfactants are present as salts along with salt forming cation common to the art, such as sodium, potassium, or ammonia. Non-soaping anionic surfactants operative herein illustratively include linear alkyl benzene sulfonates, olefin sulfonates, hydroxyl alkane sulfonates, paraffin sulfonates, ethoxylated $C_8$-$C_{24}$ alkyl ether sulfates, and di($C_1$-$C_8$ alkyl) sulfosuccinates, and combinations thereof. In addition to the non-soaping water soluble anionic surfactant, the microemulsion component of an inventive composition is intermixed with a polar organic molecule, the polar organic molecule having a hydrophobic aliphatic portion and at least one hydrophilic moiety. The anionic surfactant is typically present at 10 to 40 weight percent of the microemulsion. Typically, the molecular weight of a polar organic component of a microemulsion is between 50 and 500 atomic mass units. It is also appreciated that molecular emulsifiers as detailed above are also operative herein as the polar organic component of a microemulsion component. In addition to the molecular emulsifiers, a polar organic component operative in an inventive composition illustratively includes $C_2$-$C_{14}$ diols; glycols such as neopentyl glycol; dibasic esters such as $C_1$-$C_6$ esters of adipic, glutaric and succinic acids; and combinations thereof. The polar organic component is typically present at 50 to 75 weight percent of the microemulsion. Dibasic esters represent a preferred class of microemulsion solvents. Preferably, the non-soaping anionic surfactant is intermixed with at least two different types of polar organics in the presence of a majority phase water to form a microemulsion. Representative formulations and techniques for formation of microemulsions are illustratively detailed in U.S. Pat. Nos. 5,523,025 and 6,165,962. Optionally, terpenes or terpenoids are added to the microemulsion to facilitate soil and lipophilic resin or debris removal. Terpenes and terpenoids suitable for inclusion in a microemulsion illustratively include limonene, and turpentine spirits. An inventive microemulsion component is readily formed by mixing together: between 20-60 microemulsion total weight percent polar organics, 20-60 microemulsion total weight percent water, 10-40 percent anionic surfactant, and optionally, between 0-20 percent terpene/terpenoids. Preferably, the microemulsion constituents are chosen to afford a polar bonding value of between 2 and 3.3 along with a simultaneous hydrogen bonding value of between 4.5 and 6, as determined by Hansen solubility parameters, using the Y-MB method.

An inventive composition includes as a solvent a ketal ester solvent, alone or in combination with a microemulsion. A ketal ester solvent operative herein is preferably VOC exempt and formed by the condensation of a carboxylic acid ester with a diol. Suitable acids to undergo condensation with a diol illustratively include levulinic acid, pyruvic acid, oxaloacetate, and alpha-ketoglutaric acid. Ketalization of the ketone moiety of the acid are well known the art (Patel et al., Journal of Molecular Catalysis A: Chemical 194(1-2) 2003, 267-271). Preferably, the microemulsion constituents are chosen to afford a polar bonding value of between 5 and 8 along with a simultaneous hydrogen bonding value of between 8 and 12, as determined by Hansen solubility parameters using the Y-MB method.

An inventive composition also includes an emollient. An emollient operative herein illustratively includes hydrophobic organo-silicone-based polymers with repeating siloxane (Si—O) units and include linear, cyclic and cross-linked varieties of cyclomethicones, dimethicones, phenyl-modified silicones, alkyl-modified silicones, silicone resins, and combinations thereof; unsaturated esters or fatty esters, such as ethyl-, hexyl-stearate, isopropyl myristate, caprylic/capric triglycerides; polyols; glycerol; glycerine; cetyl alcohol; carbopol; ethoxylated castor oil; paraffin oils; lanolin; alkylene glycol or polymer formed thereof; mineral oil; wheat germ extract; jojaba extract; and combinations thereof An alkylene glycol operative herein is ethylene glycol, propylene glycol, polyethylene glycol, polypropylene glycol, a mixed poly(ethylene glycolpropylene glycol), and a combination thereof.

Typical quantities of an emollient present in the inventive composition range from 0.1-10 total weight percent with 1-6 total weight percent being preferred.

An inventive composition optionally includes one or more emulsifiers to promote phase homogeneity and storage stability of the inventive composition. It is appreciated that the emulsifiers also can facilitate the solubilization of a target soil, resin, or other substance disintegration into a soluble or colloidal form within an inventive composition. Emulsifiers operative herein are operatively limited only in being chemically-compatible and substantially nonreactive with other components of an inventive composition, and in quantities required to retain pH storage stability and phase homogeneity. Types of emulsifiers operative herein include $C_6$-$C_{12}$ alcohol ethoxide-propoxide adducts, polymeric carboxylates, and molecular emulsifiers. It is appreciated that the overall loadings of emulsifiers of the present invention and combinations thereof are somewhat variable based on specific identities; however, factors relevant in selecting the quantity of emulsifiers include quantity of microemulsion present, composition viscosity, ketal ester amount and properties. Molecular emulsifiers characterized by a molecular weight of generally less than about 500 atomic mass units include aliphatic sequences as well as hydrophilic substituents such as one or more of the moieties of hydroxyl, carboxylate, quaternary amine, and sulfonate. A molecular emulsifier operative herein illustratively includes triethanolamine, cetyl stearyl alcohol, sorbitan sesquioleate, polyoxyethylene sorbitan monopalmitate, polyoxyethylene sorbitan mono-oleate, non-ethoxylated glyceryl monostearate, cetearyl alcohol, sodium stearoyl lactylate, lecithin, and combinations thereof. Typically, a molecular emulsifier is present from 0 to 10 total weight percent with 1.2-8 total weight percent being preferred.

Optional additives to a base inventive composition that are well suited for the formation of a liquid hand cleaning composition include: fragrance compounds that are optionally present from 0.001 to 3 total percent; polyvalent metal ion salts such as magnesium oxide, magnesium sulfate, magnesium hydroxide, magnesium chloride, magnesium carboxylates, magnesium halides, magnesium nitrates, as well as aluminum, iron, calcium, and other polyvalent metal ions forming salts with these anions, the polyvalent metal ion salts are optionally present from 0 to 2 total weight percent and are well suited for improving lipophilic soil lift in water containing higher salt loadings; an antimicrobial to improve storage stability illustratively includes quaterniums, triclosan, PCMX, and other conventional antibacterials, an antimicrobial is optionally present from 0 to 2 total weight percent and preferably. between 0.005 and 1 total weight percent; a foaming agent is optionally present from 0 to 2 total weight percent and preferably, between 0.2 and 0.6 total weight percent; dibasic esters are typically present between 0 and less than 0.4 total weight percent and preferably, present at less than 0.2 total weight percent; a colorant is optionally present in an amount of from 0 to 1 total weight percent and preferably, from 0 to 0.3 total weight percent; and a pH modifying source of a mineral acid, organic acid, or hydroxide source such as sodium hydroxide or potassium hydroxide is optionally present in a quantity appropriate to adjust overall inventive composition pH to a desired value while preserving pH storage stability and phase stability thereof. An inventive composition typically has pH values range from 6 to 9 fully formulated.

Preferably, the inventive composition is impregnated or even saturated into a towel preferably when the towel is hydrophob. It is appreciated that frictional forces applied between a towel surface even if lacking an abrasive and a target surface to be cleaned is sufficient to promote soil removal or a soil film therefrom. More preferably, the towel has an abrasive adhered to at least one of the opposing surfaces thereof. A plurality of abrasive towels are readily provided in a continuous, perforated, rolled cylinder of towels or as a stack of such towels. The line of perforation presents a line of weakness by which the towels can be easily separated. The towels are inserted on-end into a selectively resealable, preferably cylindrical container, with the axis of the cylinder being aligned in an essentially vertical orientation. The inventive composition is then added to the container, preferably by pouring the same over the cylinder of towels, thereby moistening the towels with the inventive cleaning composition within the container. The capillary action associated with the void volume of the towel as discussed above causes the inventive cleaning formulation to be evenly distributed throughout the cylinder of towels.

An example of a suitable container for holding the towels is an essentially airtight lid on a cylindrical or hexahedral rectilinear container defining an interior volume, the lid can be selectively sealed, the lid having a hinged cap. The opening of the cap allows for the passage of towels from the interior of the sealed container via the opening, so individual towels can be removed from the interior container by pulling the towel and tearing the same off of the towel roll at the perforated line located between each individual towel. The opening is appropriately sized to allow for the removal of excess liquid from each individual towel as it is removed from the container. Alternatively towels are accordion folded and stacked in a hexahedral container and the top towel drawn through the lid.

In use, an individual towel is removed from the container as described above. When properly prepared, the towel contains an amount of cleanser sufficient to thoroughly cleanse the skin of the user. As the towel is rubbed on the skin, it releases the liquid cleaner and allows it to have extended contact time with the skin, and also provides for continuous cleaning without the need to apply additional cleaner. The abrasive character of the towel facilitates removal of embedded soils without leaving any abrasive residue on the skin. Residue would otherwise necessitate rinsing the skin with water after the cleansing process to thoroughly remove such abrasive residue. However, it is appreciated that an abrasive free and an inventive composition suspended are operative to clean a target surface. Thus, a waterless hand cleaner article is provided without the negative features associated with the conventional waterless hand cleaners of the prior art.

The inventive composition also assures efficient use of the cleaner, as the proper amount of cleaner is provided for each individual use. Other low viscosity liquid cleaners tend to be wasted as the low viscosity associated with such cleaners often causes them to run off of the skin. Gelatinous cleaners are also difficult to use efficiently, as the user often utilizes too little, thereby necessitating a repeated application; or too much, requiring a cloth or towel to remove the wasted excess.

Furthermore, the towel of the present invention acts not only as a medium for the cleaning formulation and as a vehicle for the abrasive ingredient, but it also serves to dry the skin after the cleanser has been used and has partially evaporated from the towel.

The present invention is further detailed with respect to the following nonlimiting examples. Unless otherwise specified, the percentages detailed herein are total weight percent of the inventive formulation.

Example 1

To 500 milliliters of municipal water is added sequentially 27 grams of $C_{12}$-$C_{15}$ non-ionic surfactant with 7 moles ethylene oxide (EO), 22 grams of a microemulsion is then added, the microemulsion being composed of 20 emulsion percent sodium di(hexyl)sulfosuccinate, 40 percent dibasic esters, and 10 microemulsion weight percent of polyethylene glycol (MW 200). With addition of the microemulsion, additional components are added including 15 grams of ISOPAR M (hydrocarbon solvent); 5 grams of butyl hydroxytoluene (BHT); 3 grams of propylene glycol; 3 grams isopropyl myristate; 2.5 grams fragrance; 4 grams of vegetable oil; and 1 gram each of lanolin, aloe vera, vitamin E oil, and jojoba oil. The volume is brought to approximately 1 liter with the addition of more municipal water and the mixture is stirred at 20° Celsius until homogeneous. The resultant composition is saturated into a towel having an abrasive adhered to a surface and constitutes an effective liquid hand cleaner able to solubilize or otherwise lift more than 0.1 grams petroleum jelly per gram of inventive hand cleaner composition from hands with 2 minutes of interworking on user hands.

Example 2

The cleaning composition of Example 1 is reformulated with 49 grams of levulinic acid based ketal in lieu of the microemulsion detailed above in Example 1 with the quantity of water being adjusted to compensate for differential in other components. A cleaning composition and abrasive article with similar properties to that of Example 1 is produced.

Example 3

The cleaning composition of Example 1 is reformulated with 25 grams of levulinic acid based ketal and 12 grams of the microemulsion in lieu of the 22 grams of microemulsion detailed above in Example 1 with the quantity of water being adjusted to compensate for differential in other components. A cleaning composition and abrasive article with similar properties to that of Example 1 is produced.

Comparative Example

In order to assess the relative cleaning ability of inventive compositions, the comparative removal of the Example 3 composition is contrasted with that of a control composition. The control composition is formulated per U.S. Pat. No. 5,683,971 preferred composition that is saturated into an abrasive towel substrate per U.S. Pat. No. 4,833,003. The composition of Example 3 and the Comparative Example afford like cleaning properties.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A hand cleaning article comprising:
   A) a cleaning composition comprising:
      i) 0.5 to 15 total weight percent of a surfactant, said surfactant being a non-ionic surfactant, an anionic surfactant, or a combination thereof;
      ii) a dibasic ester microemulsion premixed and provided as a concentrate to said composition and present from 1 to 4 total weight percent, said microemulsion comprising:
         a) a non-soaping anionic surfactant present at 10 to 40 weight percent of the microemulsion;
         b) a polar organic component present at 50 to 75 weight percent of the microemulsion and comprising at least a dibasic ester and a $C_2$-$C_{14}$ diol;
      iii) 0.1 to 10 total weight percent of at least one emollient;
      iv) 60 to 99.4 total weight percent of water; and wherein the total volatile organic content (VOC) is less than 2 total weight percent; and
   B) a medium comprising a towel presenting two opposed surfaces, said substrate having pores for absorbing and retaining said cleaning composition.

2. The article of claim 1 further comprising at least one additive of a pH adjusting material, an antioxidant, a fragrance, a dye, and a foaming agent.

3. The article of claim 1 further comprising:
   a plurality of said towels being provided in a continuous rolled cylinder, each of said plurality of said towels separated at a line of perforation; and
   a selectively sealable, evaporation resistant container having a hollow interior in which said plurality of said towels are housed, the axis of said cylinder being aligned in an essentially vertical orientation within said container, and a lid associated therewith, said lid defining an opening therein for receiving said plurality of said towels therethrough, the opening having a selectively closeable cap associated therewith.

4. The article of claim 1 wherein said VOC content is less between 0 and 1 total weight percent.

\* \* \* \* \*